United States Patent
Neumann

(10) Patent No.: US 6,277,944 B1
(45) Date of Patent: Aug. 21, 2001

(54) ALKYLATED AND/OR ARALKYLATED POLYHYDROXY AROMATIC COMPOUNDS AND PROCESSES FOR THEIR PREPARATION AND USE

(75) Inventor: Uwe Neumann, Bad Schwalbach (DE)

(73) Assignee: Solutia Germany GmbH & Co. KG, Mainz-Kastel (DE)

( * ) Notice: Subject to any disclaimer, the term of this patent is extended or adjusted under 35 U.S.C. 154(b) by 1012 days.

(21) Appl. No.: 08/493,571

(22) Filed: Jun. 22, 1995

(30) Foreign Application Priority Data

Jun. 30, 1994 (DE) ................................................ 44 22 869
Oct. 10, 1994 (DE) ................................................ 44 36 097

(51) Int. Cl.$^7$ .......................... C07C 41/06; C07C 43/20; C08G 59/06; C08G 63/133
(52) U.S. Cl. ........................... 528/98; 528/176; 528/219; 568/628
(58) Field of Search ................... 568/640, 628; 528/98, 176, 219

(56) References Cited

U.S. PATENT DOCUMENTS

| | | | | |
|---|---|---|---|---|
| 2,079,633 | * | 5/1937 | Rothrock | 260/4 |
| 2,730,436 | * | 1/1956 | Young et al. | 568/640 |
| 3,770,544 | | 11/1973 | Holt | 156/306 |
| 4,039,724 | * | 8/1977 | Gobran | 525/455 |
| 4,189,445 | * | 2/1980 | Oppenlaender et al. | 568/609 |
| 4,275,170 | * | 6/1981 | McAllister et al. | 528/155 |
| 4,359,438 | * | 11/1982 | Hoggins et al. | 264/105 |
| 4,390,680 | * | 6/1983 | Nelson | 528/97 |
| 4,594,398 | | 6/1986 | Nelson et al. | 525/531 |
| 5,300,618 | * | 4/1994 | Durairaj | 528/87 |

FOREIGN PATENT DOCUMENTS

| | | | |
|---|---|---|---|
| 1 543 512 | | 7/1969 | (DE) . |
| 1543512 | * | 7/1969 | (DE) . |
| 2330850 | * | of 1974 | (DE) . |
| 1226020 | | 3/1971 | (GB) . |
| 59-65034 | * | 4/1984 | (JP) . |

OTHER PUBLICATIONS

Derwent accession no. 74–58511V/33 for German Patent No. 1,543,512, Dorogomilowsky Chimitsch, Aug. 1974.*
Derwent accession no. 73–80871U/52 for German Patent No. 2,330,850, Reichhold–Albert Chemie A, May 1973.*
Vollmert, "Polymer Chemistry", New York, 1973.

* cited by examiner

Primary Examiner—Robert E. L. Sellers
(74) Attorney, Agent, or Firm—Foley & Lardner

(57) ABSTRACT

Alkylated and/or aralkylated polyhydroxy aromatic compounds prepared by reaction of a polyhydroxy aromatic compound (A) with an alkylene compound (B) at elevated temperature with the addition of a mixture (C) of oxalic acid and boric acid in a molar ratio of from 1:5 to 1:0, are useful, for example, as starting materials for the preparation of condensation polymers.

15 Claims, No Drawings

ALKYLATED AND/OR ARALKYLATED POLYHYDROXY AROMATIC COMPOUNDS AND PROCESSES FOR THEIR PREPARATION AND USE

BACKGROUND OF THE INVENTION

1. Field of the Invention

The present invention relates to alkylated and/or aralkylated polyhydroxy aromatic compounds and to processes for their preparation and use.

2. Description of Related Art

Polyhydroxy aromatic compounds are employed, in particular, in polymer chemistry as starting materials for the preparation of polycarbonates, polyesters, polyethers, and epoxy resins. The term polyhydroxy aromatic compounds refers hereinafter to aromatic compounds having two or more hydroxyl groups in the molecule. The aromatic compounds may be mono- or polycyclic, and as structural elements may also include any desired combinations of individual and fused rings, and divalent groups such as (thio)ether bridges, carbonyl groups, sulfonyl groups, carboxamido groups, and/or alkylene groups.

Whereas, for example, the polycarbonates and polyphthalates derived from bisphenol A are readily soluble in aromatic solvents, the solubility in aromatic solvents of the epoxy resins which are conventional in industry is low or nonexistent. The aliphatic ethers which are suitable as solvents for epoxy resins, examples of which include methoxypropanol, ethylene glycol monobutyl ether, diethylene glycol dimethyl ether, on the one hand, are considerably more expensive than conventional solvents and, on the other hand, tend to form peroxides in contact with atmospheric oxygen. They are therefore more complex to handle and constitute a safety hazard.

Attempts previously have been made to obtain modified phenols by substitution of phenols with aryl radicals or aralkyl radicals. For instance, DE-A 19 40 220 describes a process for the preparation of aralkyl phenols by reacting an aromatic vinylidene compound with a phenol, with catalysis by acids or Friedel-Crafts catalysts.

Austrian Patent AT 284 444 discloses the reactions of substituted or unsubstituted styrenes with phenols. In these reactions, the vinyl group of the styrenes is added on ortho or para to the OH group of the phenol. The reaction is in general accelerated by using Friedel-Crafts catalysts, for example, acids and metal halides. Depending on the conditions, catalysts and proportions of the reactants which are employed in this reaction, mono-, di- or tristyrenized phenols are obtained. See page 1, lines 23 to 29. Under the conditions of the Friedel-Crafts reaction, however, isomerization reactions also take place. For example, in the case of the bis- or poly (hydroxyphenyl) alkanes, the bond between the aromatic compound and the alkylene group is broken under the reaction conditions, leading to isomerization reactions. Mixtures of polyhydroxy aromatic compounds with very different substitution patterns are obtained, and in some cases phenol or other highly volatile hydroxy aromatic compounds also are given off. Depending on the temperature, duration and conditions of the reaction, highly crosslinked brittle products or rubber-like, tacky products are obtained if the hydroxy aromatic compounds obtained in this way are reacted with epichlorohydrin or with diglycidyl compounds to give epoxy resins.

For the purpose of modifying phenols as starting compounds for epoxide base structures, methods of ring alkylation have been described, for example with olefins (K.-D. Bode in Houben-Weyl: Methoden der Organischen Chemie [Methods of organic chemistry], 4th edition, Vol. 6/1c, p. 955 ff., Georg Thieme Verlag, Stuttgart 1976). The preparation of epoxides therefrom is carried out, for example, as indicated in U.S. Pat. No. 4,594,398, wherein cationic alkylation of phenol with aliphatic dienes in the presence of catalysts is followed by reaction with epichlorohydrin to give the diglycidyl ether and resulting thereby in bisepoxides being obtained. By means of these substitution reactions, alkyl groups additionally are introduced without, however, improving the solubility in aromatic hydrocarbons. The reaction products are not uniform structures, but represent mixtures of polyhydroxy aromatic compounds with various substitution patterns and a varying number of hydroxyl groups in the molecule.

SUMMARY OF THE INVENTION

It is therefore an object of the present invention to modify polyhydroxy aromatic compounds in such a way that the solubility in aromatic solvents of the polycondensation products prepared therefrom is improved, while retaining the otherwise good level of properties of polymers prepared therefrom.

It is also an object of the invention to find a process for alkylation and aralkylation which can be applied to the above-mentioned polyhydroxy aromatic compounds and which leads to uniform products without rearrangement and without elimination of phenol(s).

It is also an object of the invention to provide polyhydroxy compounds of improved solubility, and to provide polycondensation polymers prepared from such compounds.

In accordance with these and other objects, there is provided a process for the preparation of alkylated and/or aralkylated polyhydroxy aromatic compounds comprising reacting a polyhydroxy aromatic compound (A) with an alkene and/or aralkene compound (B) at a temperature above room temperature in the presence of a mixture (C) of oxalic acid and boric acid in a molar ratio of from 1:5 to 1:0.

In accordance with these and other objects of the invention, there also is provided an alkylated and/or aralkylated polyhydroxy aromatic compound obtained by the process described above.

In accordance with other aspects of the invention, there are provided condensation polymers, such as polyesters, polycarbonates, epoxy resins, and aromatic polyethers, prepared from alkylated and/or aralkylated polyhydroxy aromatic compounds as described above.

Further objects, features and advantages of the present invention will become apparent from the detailed description of the preferred embodiments that follows.

DETAILED DESCRIPTION OF THE PREFERRED EMBODIMENTS

In the experiments to achieve the objects on which the invention is based, it was found that formic acid, acetic acid and higher carboxylic acids, alone or mixed with boric acid, possess no catalytic activity for the alkylation and aralkylation reaction. In spite of this, it surprisingly was found by the present inventors that the use of oxalic acid and boric acid provides alkylated and aralkylated polyhydroxy aromatic compound.

The invention provides a process for the preparation of alkylated and aralkylated polyhydroxy aromatic compounds by reaction of a polyhydroxy aromatic compound (A) with an alkene compound (B) at elevated temperature with the addition of a mixture (C) of oxalic acid and boric acid in a molar ratio of from 1:5 to 1:0, preferably from 1:2 to 1:0.1 and, in particular, from 1:1 to 1:0.5.

The invention also provides the alkylated and/or aralkylated polyhydroxy aromatic compounds prepared by this process.

The reaction can be carried out in any desired manner, for example, in the melt (bulk process) or in an inert, high-boiling solvent. These solvents have boiling temperatures of at least 80° C.

The reaction is carried out at any desired elevated temperature, that is, a temperature above room temperature which is, for example, at a temperature of from 80 to 180° C., preferably from 100 to 170° C. and, with particular preference, from 120 to 160° C.

In order to avoid oxidative degradation of the starting materials and products, the reaction preferably is carried out under a protective gas, such as nitrogen and/or argon. It also is possible to work under pressure, for example, if low-boiling starting materials are employed.

Any desired polyhydroxy aromatic compounds or mixtures thereof may be used. Polyhydroxy aromatic compounds which are particularly suitable for the invention are dihydroxy and trihydroxy aromatic compounds. Any known compounds of these types are useful.

Examples of suitable dihydroxy aromatic compounds include, but are not limited to, bis(4-hydroxyphenyl) (cyclo)alkanes such as 2,2-bis(4-hydroxyphenyl)propane, bis(4-hydroxyphenyl)methane and -ethane, 1,1-bis(4-hydroxyphenyl)cyclohexane, the corresponding compounds derived from naphthol, higher polyhydroxy aromatic compounds such as 1,4-bis(4'-hydroxycumyl)benzene, the dihydroxybenzene and dihydroxynaphthalene isomers, dihydroxybiphenyl, dihydroxydiphenyl ethers, dihydroxybenzophenone, dihydroxydiphenyl sulfide and dihydroxydiphenyl sulfone. Preferably used are dihydroxy aromatic compounds selected from bisphenol A, bisphenol F, hydroquinone, resorcinol, and dihydroxynaphthalene. These polyhydroxy aromatic compounds may be employed individually or in mixtures.

Any desired alkene and/or aralkene compound or mixtures of such compounds are useful as the alkene or aralkene compound (B). Examples of alkene compounds which are suitable for the invention include, but are not limited to, linear, cyclic and branched olefins having from 4 to 16 carbon atoms, such as 1-butene, 2-butene, 1-hexene, 1-octene, 2-ethyl-1-hexene, 1-decene, 1-dodecene, diolefins such as 1,3-butadiene, 1,3-hexadiene, 1,5-hexadiene, norbornene, isoprene, and cyclic diolefins such as cyclopentadiene and dicyclopentadiene. These compounds may be employed individually or in a mixture. When using lower olefins such as butene it is advantageous to employ mixtures of such olefins with styrene or with other alkenylaromatic compounds.

Examples of alkenylaromatic compounds which are suitable for the compound (B) of the invention include styrene and homologs thereof such as α-methylstyrene and the isomeric vinyltoluenes and also the technical-grade isomer mixture thereof, the isomeric ethylstyrenes, indene, and halogenated styrenes such as mono- and dichlorostyrene compound (B). These compounds may be employed individually or in a mixture with any desired alkene or aralkene compounds.

The catalyst mixture (C) is used in amounts effective to give the desired alkylated or aralkylated product. For example, 0.5 to 10% of mixture (C) by weight of starting materials (A) and (B) can be used.

The alkylated and/or aralkylated compounds according to the invention can be used in any desired manner, for example, as a polyhydroxy component used to prepare condensation polymers such as, for example, polyesters, polycarbonates, aromatic polyethers and epoxy resins, in place of or as a mixture with conventional polyhydroxy compounds. The preparation of such condensation polymers is described, i.a. in Vollmert, Polymer Chemistry, New York, 1973. The use of the compound of the invention has an influence on characteristic properties of the resulting polymers, for example, solubility, glass transition temperature and crystallinity. In this context, small amounts of the polyhydroxy aromatic compounds according to the invention added to those which are usually employed are frequently sufficient to bring about marked shifts in the pattern of properties.

The examples which follow describe the invention in more detail. The examples are for illustrative purposes only, and do not limit the invention.

EXAMPLE 1

200 g of bisphenol F are heated under nitrogen to 120° C. 2.2 g of oxalic acid dihydrate and 1.2 g of boric acid are added. A total of 104 g of styrene are added slowly dropwise through a dropping funnel at a rate such that the temperature does not exceed 160° C. At 160° C. stirring is carried out for a further two hours and then the mixture is cooled. According to analysis, the reaction product contains on average one phenylethyl group per molecule of bisphenol F.

EXAMPLE 2

228 g of bisphenol A are heated under nitrogen to 160° C. 4.2 g of oxalic acid dihydrate and 1 g of boric acid are added. A total of 208 g of styrene are added dropwise at a rate such that the temperature of the reaction material is maintained at between 155 and 165° C. When addition is complete, stirring is carried out for a further two hours at 160° C. According to analysis, the reaction product contains on average two phenylethyl groups per molecule of bisphenol A.

EXAMPLE 3

110 g of resorcinol are heated under nitrogen to 120° C. 2.2 g of oxalic acid dihydrate and 0.5 g of boric acid are added. A total of 130 g of styrene are added dropwise at a rate such that the temperature of the reaction material is maintained at between 120 and 130° C. When addition is complete, stirring is carried out for a further two hours at 160° C. According to analysis, the reaction product contains on average 1.25 phenylethyl groups per molecule of resorcinol.

EXAMPLE 4

114 g of bisphenol A are heated under nitrogen to 160° C. 1 g of oxalic acid dihydrate and 0.8 g of boric acid are added. A total of 52 g of styrene are added dropwise at a rate such that the temperature of the reaction material is maintained at between 155 and 165° C. When addition is complete, stirring is carried out for a further two hours at 160° C. According to analysis, the reaction product contains on average one phenylethyl group per molecule of bisphenol A.

EXAMPLE 5 (COMPARATIVE)

114 g of bisphenol A are heated under nitrogen to 160° C. 2 g of anhydrous aluminum chloride are added. A total of 52 g of styrene are added dropwise at a rate such that the temperature of the reaction material is maintained at between 155 and 165° C. At this point the odor of phenol is evident. When addition is complete, stirring is carried out for a further two hours at 160° C. The resulting product has brown discoloration and a nonuniform composition.

While the invention has been described with reference to certain preferred embodiments, numerous modifications, alterations, and changes to the preferred embodiments are possible without departing from the spirit and scope of the invention.

What is claimed is:

1. A process for the preparation of an alkylated or aralkylated polyhydroxy aromatic compound comprising reacting a polyhydroxy aromatic compound (A) with an alkene or aralkene compound (B) at a temperature above room temperature in the presence of a mixture (C) of oxalic acid and boric acid in a molar ratio of oxalic acid to boric acid of from 1:5 to 1:0.1.

2. A process for the preparation of an alkylated or aralkylated polyhydroxy aromatic compound as claimed in claim 1, wherein the molar ratio is from 1:2 to 1:0.1.

3. A process for the preparation of an alkylated or aralkylated polyhydroxy aromatic compound as claimed in claim 1, wherein the molar ratio is from 1:1 to 1:0.5.

4. A process for the preparation of an alkylated or aralkylated polyhydroxy aromatic compound as claimed in claim 1, wherein the reaction is a bulk process carried out in the melt.

5. A process for the preparation of an alkylated or aralkylated polyhydroxy aromatic compound as claimed in claim 1, wherein the reaction is carried out in an inert, high-boiling solvent.

6. A process for the preparation of an alkylated or aralkylated polyhydroxy aromatic compound as claimed in claim 1, wherein the reaction is carried out at a temperature of from 80 to 180° C.

7. A process for the preparation of an alkylated or aralkylated polyhydroxy aromatic compound as claimed in claim 1, wherein component (A) comprises one or more of dihydroxy and trihydroxy aromatic compounds.

8. A process for the preparation of an alkylated or aralkylated polyhydroxy aromatic compounds as claimed in claim 1, wherein component (A) comprises a dihydroxy aromatic compound selected from the group consisting of bisphenol A, bisphenol F, hydroquinone, resorcinol, and dihydroxynaphthalene.

9. A process for the preparation of an alkylated or aralkylated polyhydroxy aromatic compound as claimed in claim 1, wherein component (B) comprises one or more of alkene aromatic compounds or diolefins or mixtures of these compounds.

10. A process for the preparation of an alkylated or aralkylated polyhydroxy aromatic compound as claimed in claim 1, wherein component (B) comprises styrene.

11. A process for the preparation of an alkylated or aralkylated polyhydroxy aromatic compound as claimed in claim 1, wherein component (B) comprises vinyltoluene.

12. A process for the preparation of an alkylated or aralkylated polyhydroxy aromatic compound as claimed in claim 1, wherein 0.5 to 10% of mixture (C) are used based on the mass of the starting materials (A) and (B).

13. A process for the preparation of an alkylated or aralkylated polyhydroxy aromatic compound as claimed in claim 1, wherein the reaction is conducted under a protective gas.

14. A process for the preparation of an alkylated or aralkylated polyhydroxy aromatic compound as claimed in claim 1, wherein the reaction is conducted under a protective gas selected from the group consisting of nitrogen and argon.

15. A process for the preparation of an alkylated or aralkylated polyhydroxy aromatic compound as claimed in claim 1, wherein the process gives uniform products without rearrangement and without elimination of phenols.

\* \* \* \* \*